United States Patent [19]

Meller

[11] Patent Number: 4,561,845
[45] Date of Patent: Dec. 31, 1985

[54] ILLUMINATION FOR DENTAL DRILLS

[76] Inventor: Moshe Meller, 20 Rachel St., Haifa 34402, Israel

[21] Appl. No.: 571,861

[22] Filed: Jan. 18, 1984

[30] Foreign Application Priority Data

Jan. 30, 1983 [IL] Israel ............................. 67784

[51] Int. Cl.$^4$ ........................... A61C 1/00; A61C 3/00
[52] U.S. Cl. .................................................... 433/29
[58] Field of Search ................... 433/29, 114, 133

[56] References Cited

U.S. PATENT DOCUMENTS

| 3,109,238 | 11/1963 | Marks | 433/29 |
| 4,184,196 | 1/1980 | Moret et al. | 433/29 |
| 4,375,964 | 3/1983 | Knopp et al. | 433/29 |

FOREIGN PATENT DOCUMENTS 1068425  11/1959  Fed. Rep. of Germany ........ 433/29

Primary Examiner—Robert Peshock
Attorney, Agent, or Firm—Henry Sternberg; Bert J. Lewen

[57] ABSTRACT

A dental hand-piece having a fluid powered tool and a self-contained light source for illuminating the region of the work tip of the tool. The sleeve portion of the hand piece defines a substantially cylindrical cavity for containing a battery and the conduits for supplying the necessary fluid to the dental tool extend generally longitudinally of the sleeve member, exteriorly of the battery in the cavity.

19 Claims, 7 Drawing Figures

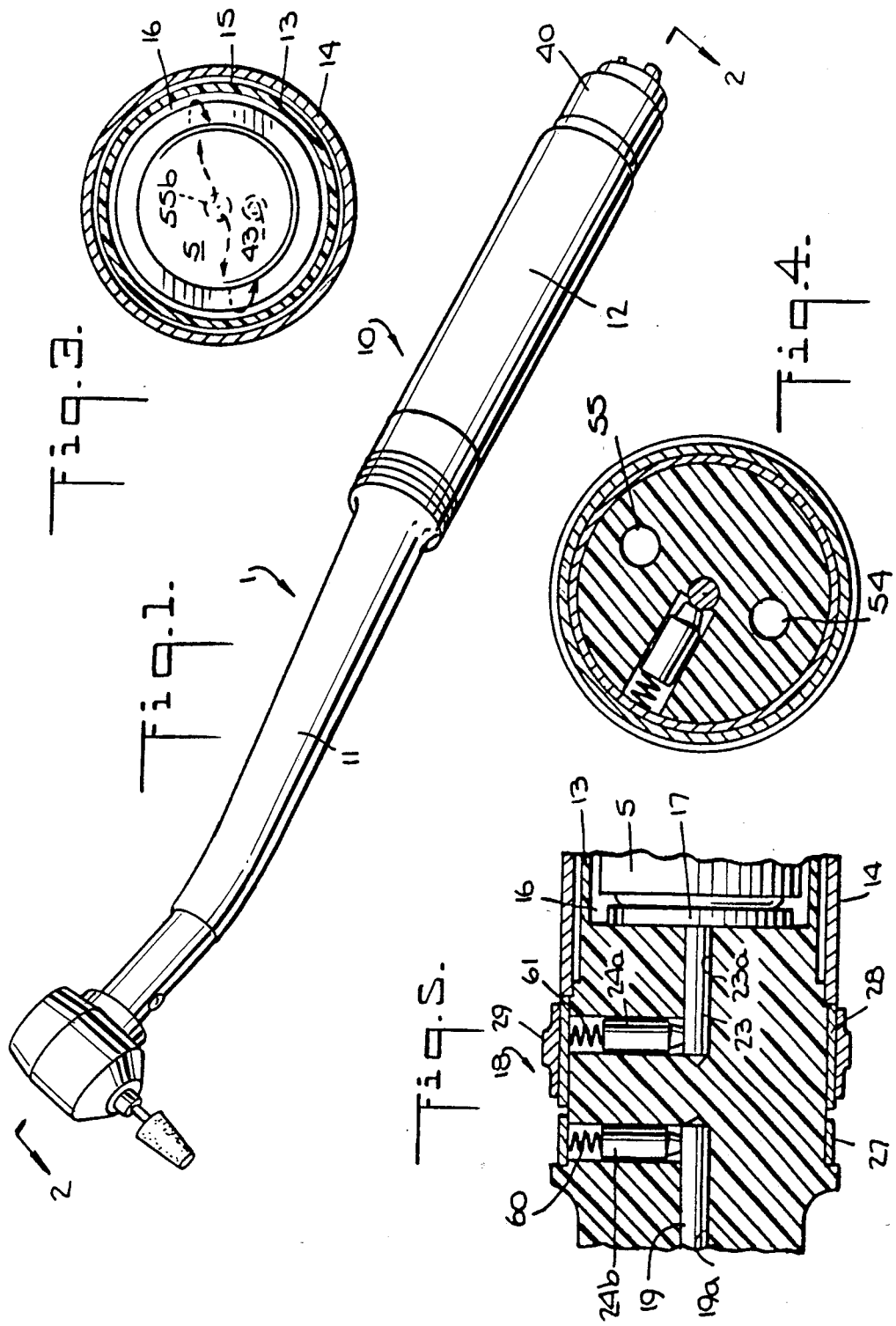

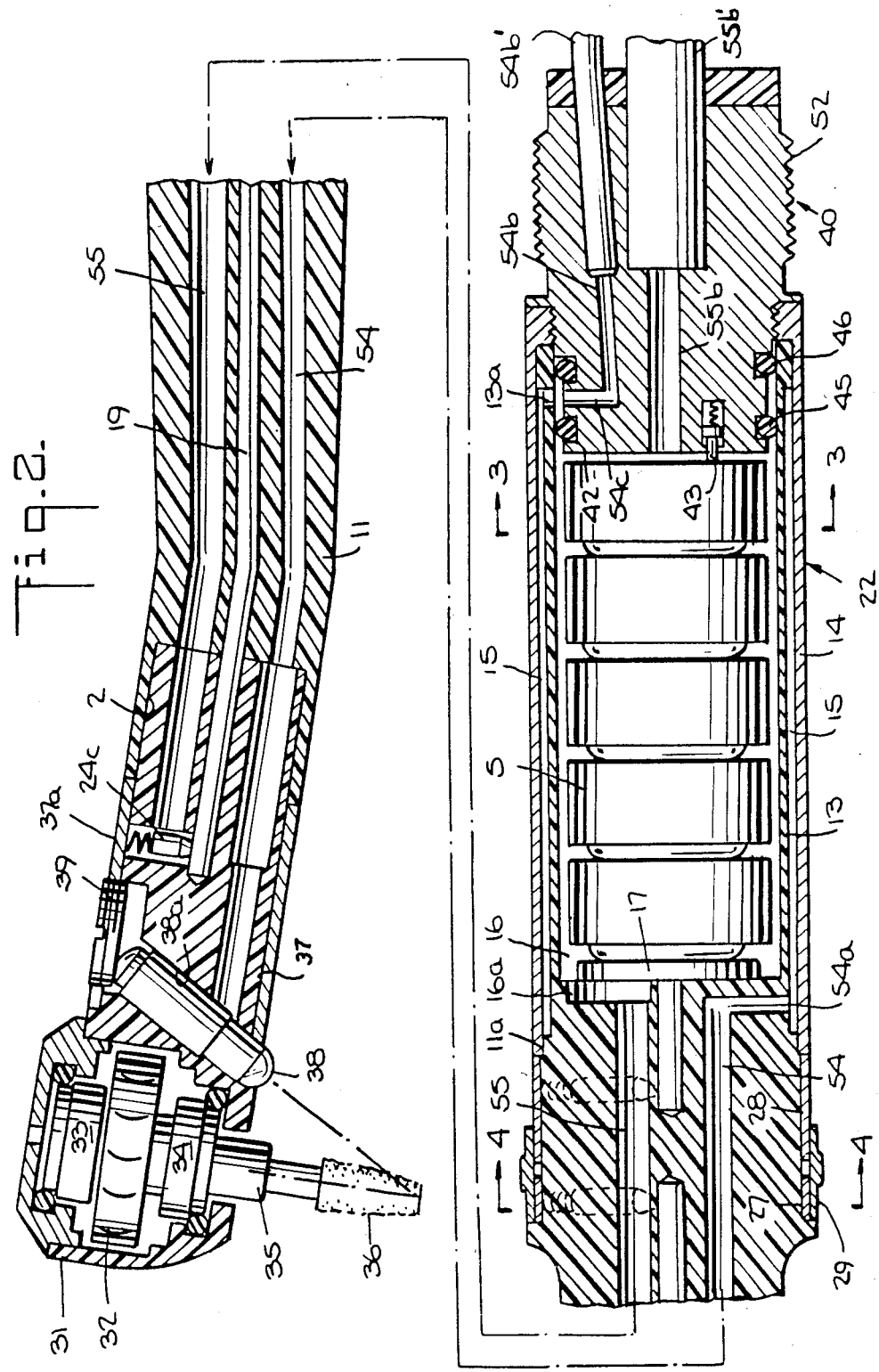

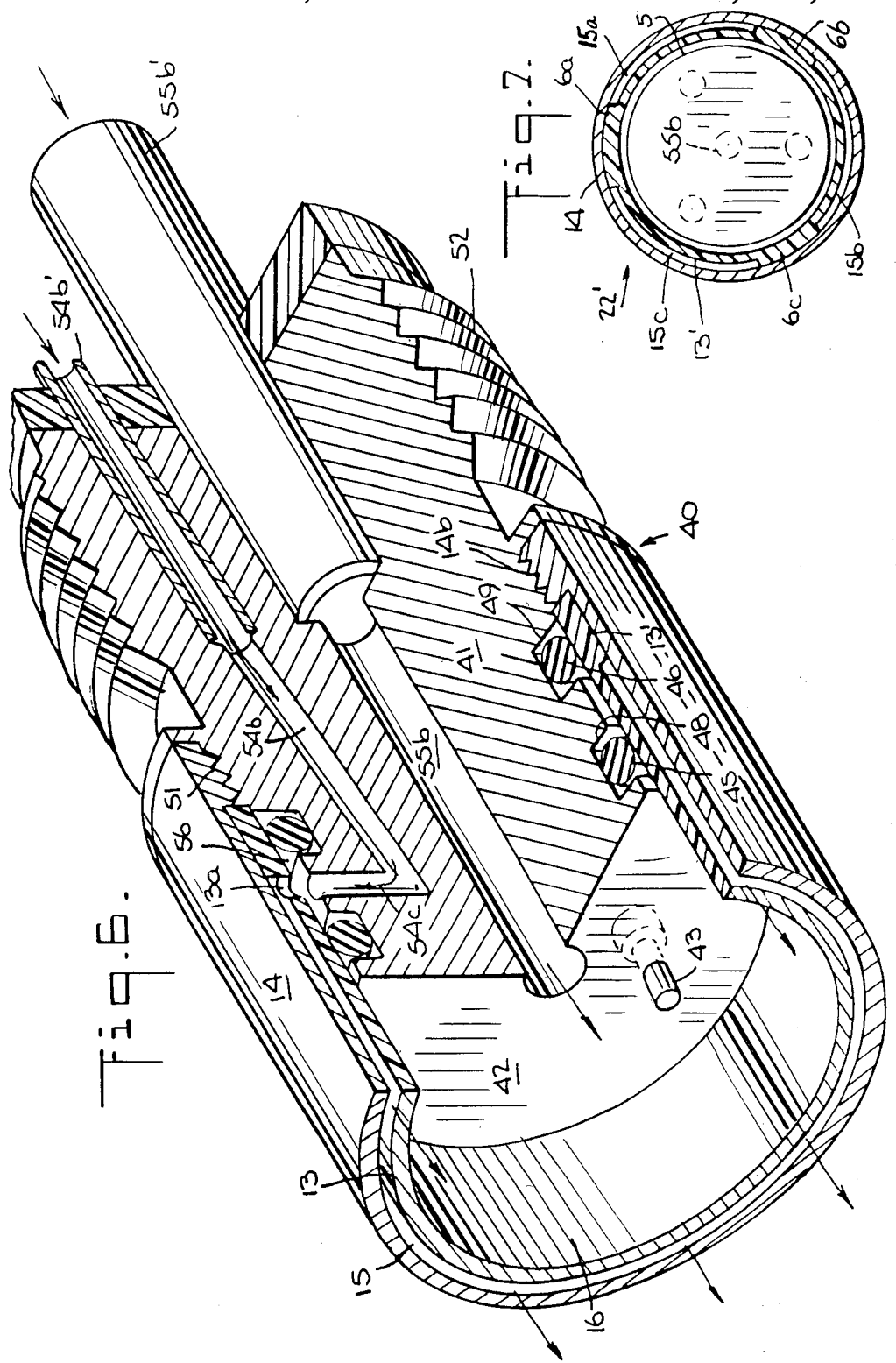

ILLUMINATION FOR DENTAL DRILLS

The invention relates to dental drills, and more specifically to means for directly illuminating the area in the mouth which is being worked on.

BACKGROUND OF THE INVENTION

Dental work on teeth and other parts of the oral cavity has to be very accurately and delicately performed. It is essential that the dental surgeon, since he works in an otherwise dark cavity, has available to him a strong light beam which he can direct onto the spot which he is drilling or grinding and that such light should be of a kind which is not obstructed by the dentist's hands or head.

Existing equipment used by dentists to direct light rays from an external light source into the mouth of the patient conventionally requires the use of a small mirror. This is quite inconvenient since it occupies both of the dentist's hands, one hand holding the drill and the other hand holding the mirror. Furthermore, there is in the use of this method the danger of the obstruction of the light path by the dentist's hands or body.

In an effort to overcome the aforesaid problems a form of direct illumination was introduced a few years ago using optical fibers for transferring a light beam from an external source to a point just above the burr in the dental handpiece. In the known apparatus the light source is generally on the main frame of the drilling apparatus and has its beam directed into the receiving end of a flexible fiber-optic bundle. This flexible fiber-optic bundle extends from the stationary light source to the connector to which the handpiece is connected. A second fiber-optic bundle then extends through the handpiece to a point above the burr for directing the light beam toward the point of the burr. The connector required for connecting the removable handpiece, with its optical fibers, to the remainder of the drill apparatus must, of course, be of special construction since the optical fibers of the two bundles must be connected to one another in such a manner as to permit the passage of light through the connection thus formed. It has been found that this type of apparatus suffers from a number of disadvantages: First is the high cost of known fiber-optic devices. Second, the continuous flexing of the first fiber-optic bundle in response to movement of the handpiece results in elastic deformation along the length of the fibers, which in turn may result in fluctuations in the light intensity of the beam at the very time when drilling is taking place. Furthermore, use of fiber optics requires standardization of equipment since only handpieces equipped with the aforesaid special connector can be used in the installation with drill apparati which themselves must contain a light source and the aforesaid fiber optic capability.

It is therefore an object of the present invention to provide a dental handpiece which will overcome the disadvantages mentioned above.

It is another object of the present invention to provide a dental handpiece which has a source of illumination for illuminating the work area with a light beam which does not fluctuate in intensity, which does not risk being obscured by the dentist's hand or other parts of his body or by parts of the patient's body and which does not require a special connector.

It is a still further object of the present invention to provide a dental handpiece which is capable of illuminating the work area yet does not require a special drill apparatus and thus may be interchangeably used with drill apparati of conventional construction.

It is a concomitant object of the present invention to provide a dental handpiece which incorporates both a source of illumination and a built-in power source for such illumination so as to eliminate the need for fiber-optics.

One of the serious problems of positioning a power source at the interior of a dental handpiece is the presence there of the plurality of ducts for water and compressed air extending through the conventional handpiece and the necessity for maintaining nevertheless the size of the handpiece, particularly the outer peripheral size thereof, approximately the same as that of conventional handpieces which the dentist is used to handling. Thus, the relatively small diameter body portions of conventional handpieces have air and water passages extending longitudinally therethrough and occupying substantial portions of the cross-sectional space therein. It is therefore the principal object of the present invention to position a self-contained illuminating means in the dental handpiece without substantially increasing the outer peripheral size thereof and yet without interfering with the passage of gaseous and liquid fluids therethrough.

SUMMARY OF THE INVENTION

In its preferred form the device according to the present invention is used in connection with high speed drills where the burr, or dental tool, is mounted on a common shaft with an air driven turbine wheel mounted in the drill head proper. The device is simple and less costly than the hitherto known illuminating equipment and dispenses with hand held mirrors, long optical fibers and special connectors for optical fibers. The self-contained illumination means for the dental handpiece according to the invention comprises an electric voltage source positioned inside a handpiece of generally conventional size, a light source positioned on the handpiece close to the burr so as to direct the light beam onto the spot being drilled and electric conductor means connecting the light source to the voltage source.

Preferably, the light source is in the form of a small incandescent bulb positioned at an angle on the dental handpiece so that its light beam is directed toward the tip of the burr. The electric voltage source is preferably in the form of a plurality of electric cells located in a chamber in the body portion of the handpiece.

According to the preferred embodiment of the invention a dental handpiece comprises an elongated body member, a head member at one end of said body member adapted to hold a dental tool having a working tip, connector means at the other end of said body member for coupling the handpiece to a conventional drill apparatus and illuminating means on one of said members for illuminating said tip. The body member includes sleeve means defining a central cavity adapted to contain an electric power source and electrically conductive means connecting said electric power source with said illuminating means. The sleeve means have one or a plurality of circumferentially distributed fluid ducts extending generally longitudinally therethrough exteriorly of said cavity, and the connector means and said one end of said body member each have a solid portion containing at least one bore extending generally longitudinally therethrough and communicating with a corresponding one or ones of said ducts for conveying fluids around said cavity between said head member and said connector means.

According to the present invention conventional connector fittings for compressed air and water are provided in the connector member at the rear of the handpiece, and are brought to the head portion by ducts inside the handpiece body member which latter is of conventional shape and size.

A feature of the invention is the provision of an annular space around the periphery of the chamber containing the source of electricity. This space may form a single annular duct or may be divided into a plurality of circumferentially distributed ducts separated from one another by longitudinally extending ribs so that water and compressed air may be conveyed, through a plurality of adjacent ducts, longitudinally past the electric power cells.

The components of the handpiece are preferably of an aluminum alloy which is preferably anodized on all but a select few outer and inner surfaces thereof. The anodizing results in a surface layer which is hard, abrasion resistant and insulates against electric current transmission. By selectively omitting anodize from some contacting surfaces between connected portions of the handpiece, a defined path for electric current from one portion of the handpiece to another is provided.

BRIEF DESCRIPTION OF THE DRAWINGS

The invention will be better understood from the following specific description given in conjunction with the accompanying drawings in which:

FIG. 1 is a perspective view of a handpiece according to the present invention for a high-speed dental drill showing fluid conduits connected to the rear thereof.

FIG. 2 is a longitudinal section along line 2—2 of FIG. 1, showing the ducts for air and water extending through the handpiece.

FIG. 3 is a transverse section along line 3—3 of FIG. 2 showing the ducts for air and water in the region of the battery compartment.

FIG. 4 is a transverse section along line 4—4 of FIG. 2 showing a detail of a portion of the electrical connection for the switch in the body member.

FIG. 5 is a longitudinal sectional view of a portion of the body member of the present invention.

FIG. 6 is a perspective, partly sectional, view of the connector and a portion of the rear of the body member according to FIG. 2.

FIG. 7 is a transverse sectional view similar to the FIG. 3 view, of another embodiment of the invention.

DETAILED DESCRIPTION OF THE INVENTION

Referring now to FIG. 1 and FIG. 2 of the drawings, the handpiece 1, according to the preferred embodiment of the invention, consists of a body member 10 having a frontal portion 11, a working head member 30 connected to the frontal portion 11 and a connector 40 connected to the rear portion 12 of said body member 10. The frontal portion 11 is generally of solid cylindrical construction while the rear portion 12 is generally of hollow cylindrical construction so as to form a cavity or compartment 16 for housing batteries.

The head member 30 includes a housing 31 having an extension 37 for attaching the head member to the frontal portion 11. Housing 31 contains a turbine means 32 comprising a centrifugal turbine wheel driven by compressed air supplied from the body member 10 to which the working head is attached. This turbine means is shown diagrammatically only since it may be of conventional design. Neither the air inlet nozzle nor the outlet nozzle for the turbine 32 are shown in the drawings since these may also be of conventional design. The housing extension 37 of head member 30 is received in a forward opening cavity 2 at the front end of the body member 10 in conventional manner. Turbine 32 is provided with an internal chuck 35 and is rotatably mounted in bearings 33, 34. A burr 36 is interchangeably gripped in the chuck. An incandescent bulb 38, which forms part of an illuminating means, is preferably mounted in the extension 37 of the head member 10 in an obliquely drilled bore 38a so that it will illuminate the tip of the burr 36. Preferably the bulb 38 is elongated and fits snugly into the bore 38a. Bore 38a has a first open end in proximity to but spaced from the shaft of the dental tool 36 such that the bulb 38 whose light emitting end protrudes through said open end of the bore 38a will preferably direct its beam of light to intersect the axis of the dental tool or burr 36 at a distance from the outer surface of the head member 30 which distance is chosen such that it is the average distance from the head member to burr tip of the dental tools most commonly used by dentists in high speed dental handpieces.

The frontal portion 11 has, in the preferred embodiment shown in FIG. 2 and FIG. 4, two bores 54 and 55, extending substantially longitudinally therethrough, a cylindrical cavity 2 at the head end thereof and a rear portion in the form of an integral cylindrical sleeve, i.e. inner sleeve 13 extending rearwardly thereof. Inner sleeve 13 and concentric, spaced, outer sleeve 14, which surrounds it, together form sleeve means 22 defining the compartment, or chamber 16 at the rear portion 12 and define a longitudinal annular space or duct, 15 extending around, and exteriorly of, the chamber 16.

The solid cylindrical frontal portion 11 of the body member 10 is drilled to form the axially extending bores 54 and 55. Bore 54 communicates at its rear end, through a corresponding radial bore, 54a with the longitudinal duct 15 and at its front end with the working head member 30. The bore 55 communicates at its rear with a slot 16a located at the front end of, and opening into, the compartment 16. Bore 55 communicates at its front end with the working head 30 for supplying to the turbine inlet nozzle (not shown) compressed air which has passed through the compartment 16.

Connector 40, best shown in FIG. 6, is also preferably a solid cylindrical member which preferably has two longitudinal bores 54b and 55b. Bore 54b communicates with the corresponding longitudinal duct 15 via radial bore 54c while the bore 55b communicates at its front end directly with the compartment, or cavity 16, which latter preferably contains a source of electric power. At their rear ends the bores 54b and 55b are connected to short tubes 54b' and 55b' respectively which are adapted to connect in conventional manner to connecting tubes in the conduit extending from the main frame of a conventional drill apparatus. Outer tubular sleeve 14 is attached to the frontal portion 11 by being press-fitted around cylindrical shoulder 11a at the rear of said frontal portion. Inner sleeve 13, also of tubular shape, is integral with a stepped portion at the rear of the frontal portion 11 and extends rearwardly therefrom. The inner sleeve 13 is provided with at least one radial bore 13a which serves as a conduit for fluid between the duct 15 and the inlet passage 54b', 54b and 54c of connector means 40 forming one fluid inlet of the handpiece. The inner sleeve 13 has, at its rear end, an outer flange 13' press-fitted into outer sleeve 14, leaving exposed the internal screw thread 14b at the rearmost portion of outer sleeve 14. The front end of the connector 40 is in the form of a cylindrical grooved plug 41 which is fitted into the bore of tubular sleeve 13, while its rear portion, of larger diameter, is provided with external screw thread 52 adapted for attachment of the dental handpiece to the conventional connector (not shown) of a conventional dental drilling apparatus (not shown). An external screw thread 51 on connector 40 intermediate said front and rear portion thereof is adapted to mate with internal thread 14b of outer sleeve 14 when the connector plug 41, is received in the bore of inner sleeve 13. Sealing rings in the form of O-rings 45 and 46 are positioned, respectively, in circumferential grooves 48 and 49 provided on the outer surface of plug 41 so as to form fluid seals between the plug 41 and the inner sleeve 13 when the connector plug is received in the bore of the inner sleeve. Radial bore 54c at the forward end of bore 54b communicates with a peripheral annular channel 56, formed between the connector plug 41 and inner sleeve 13 and bounded on opposite sides by the O-rings 45 and 46 respectively.

According to the preferred embodiment the electric power source for illuminating incandescent bulb 38 is in the form of five button-shaped batteries 5, preferably model No. 675 manufactured under the name "Premium" under U.S. Pat. No. 3,922,178 and axially aligned in series in the cavity 16. The inner diameter of sleeve 13 is such that it at least slightly exceeds the outer diameter of the batteries 5. Connector member 40 is removable at the threads 14b, 51 for opening chamber 16 at its rear so that the batteries may be placed therein. The batteries are pressed onto an electrical contact button 17 at the opposite end of cavity 16 by screwing the male thread 51 on the connector into the female thread 14b at the rear of outer sleeve 14. Contact button 17 is insulated from the rest of body member 10 by providing anodize on all the mating surfaces between the two. A spring-loaded plunger 43 extending forwardly from the front face 42 of connector 40 is adapted to press forwardly against the rear of the rearmost battery 5 in the chamber 16 so as to maintain electrical contact between the front terminal of the batteries and contact button 17 and between the rear terminal of the batteries and the plunger 43. This plunger 43 is arranged with a back stop so that it will always maintain the rear terminal of the rear battery spaced from the front face 42 of the connector 40 so as to provide a space for the air from air inlet bore 55b to enter the battery compartment 16. Contact button 17 has a rod 23 projecting forwardly therefrom into a short longitudinal bore 23a in frontal member 11 and arranged to form an electrical path via a coil spring loaded plunger 24a to the switch means 18 (see FIG. 5) and from there through a second coil spring loaded plunger 24b to an electrically conducting rod 19 in a bore 19a. Bores 19a and 23a are anodized at the interior surfaces thereof and, extend centrally of the frontal body section 11. Rod 19 extends to the vicinity of the bulb 38. A third coil spring loaded plunger 24c in a radial bore provides an electrical connection between the front end of rod 19 via a portion 37a of the head member 30 and a screw closure 39 which covers the rear opening of bore 38a and forms an electrical connection with the rear terminal of bulb 38. The second terminal of the bulb 38 is in conductive contact with the wall of the bore 38a and thereby electrically connected via the frontal body section 11, through the outer sleeve 14, the screw connection 14b, 51, the connector 40 and the conductive plunger 43, to the rear terminal of the rearmost of the batteries 5. The switch 18 allows for the closing and opening of the electrical connection between the bulb 38 and the source of electric power 5 and is provided on the outside of the frontal portion 11 so as to be readily actuated by the thumb of the dentist. The switch 18 is preferably in the form of a slideable collar 29 positioned around a pair of axially spaced annular rings 27, 28 on which the collar 29 slides so as to bridge the gap between the rings 27, 28 when the switch is in the "on" position (FIG. 2). Each conductor ring 27, 28 is insulated, by anodized surfaces, from the body member 10 on which it is positioned and is electrically conductively connected with the radially oriented coil springs 60 and 61 respectively.

According to another embodiment of the invention seen in FIG. 7, annular space 15 is separated into three fluid conveying ducts 15a, 15b and 15c, circumferentially distributed therein. These ducts are formed by, for example, three outwardly projecting longitudinal ribs 6a, 6b and 6c on the periphery of inner sleeve 13', which serve not only to divide the space between the inner and outer sleeves into the three longitudinal ducts but also act as reinforcing and spacing members for maintaining the integrity of sleeve means 22'. It will readily be seen that additional such ribs can be used to provide additional ducts around the compartment 16.

Preferably outer sleeve 14 is press-fitted around the periphery of the ribs on inner sleeve 13' so as to tightly seal the ducts from one another.

It will be understood that the arrangement of the bores and ducts is arbitrary and that additional bores and corresponding ducts may be used in both the body section and the connector, so long as the ducts extend between the outer and inner sleeves which surround the voltage source. Also, it will be understood that the arrangement of the ducts in the annular space between the inner and outer sleeves may be modified if desired. For instance, instead of providing the inner sleeve with outwardly projecting ribs, the outer sleeve may be provided with inwardly projecting ribs. According to one embodiment of the invention (not shown) four longitudinal ducts are provided in the annular space 15 and these communicate with four longitudinal bores in each of the connector member and the body member. The conduits formed by these bores and ducts are adapted to carry air and water, one of them conveying compressed air to and a second one conveying spent air from the turbine, the third one conveying water for spraying, and the fourth one conveying air for chip blowing.

When the incandescent bulb 38 is mounted in obliquely drilled bore 38a, its rear terminal contacts screw cover 39, while its body is in conductive contact with the frontal body member. Preferably the bulb is Model No. 3026-10 manufactured by Micro Gluhlampen Gesellschaft.

In operation, preferably, compressed air is supplied to the battery compartment 16 through bore 55b. This air passes around the batteries 5 and leaves the chamber 16 through the slot 16a which communicates with the bore 55 which conveys it to the turbine wheel through a nozzle (not shown). The spent air from the turbine is preferably exhausted to the atmosphere. Alternatively the spent air may be conveyed back through the handpiece, for discharge, through a duct as for example duct 15a in FIG. 7 and thru corresponding bores (not shown) in the frontal portion 11 and in connector 40 similar to the bores 54 and 54b, respectively. Preferably the passage formed by the annular duct 15 cooperating with bores 54 and 55 is used to convey water to the burr through a spray nozzle (not shown).

From the foregoing it is evident that a self-contained means for illumination, i.e., a source of light, an electric power source, and electrically conductive means connecting them, can now be incorporated in a dental handpiece of conventional size without interfering with the conveyance of the required fluids therethrough.

While there have been described what are presently considered the preferred embodiments of this invention, it will be obvious to those skilled in the art that various changes and modifications may be made therein without departing from the invention, and it is therefore aimed to cover all such changes and modifications as fall within the true spirit and scope of the invention.

What is claimed is:

1. A dental hand-piece comprising:
   (a) an elongated body member,
   (b) a head member at one end of said body member adapted to hold a dental tool having a movable working tip,
   (c) connector means at the other end of said body member for coupling the hand-piece to a conventional drill apparatus,
   (d) illuminating means on one of said members for illuminating said tip,
   (e) said body member including sleeve means defining a generally longitudinally extending generally cylindrical cavity having a diameter of sufficient size so as to be adapted to contain a battery electric power source of a cross-sectional size approximating a major part of the cross-sectional area of said body member and electrically conductive means for connecting such battery with said illuminating means,
   (f) said sleeve means having at least one fluid duct extending generally longitudinally therethrough exteriorly of said cavity for supplying fluid to said movable working tip for imparting motion thereto,
   (g) said connector means and said one end of said body member each having a solid portion containing at least one bore extending generally longitudinally therethrough and communicating with said duct for conveying fluid around said cavity between said head member and said connector means.

2. The dental handpiece of claim 1, wherein said sleeve means comprises a plurality of said ducts circumferentially distributed therein and each said solid portion contains a plurality of said bores communicating with corresponding ones of said ducts.

3. The dental handpiece of claim 1, wherein said duct has, in transverse cross-section, a width which is substantially greater than the depth thereof.

4. The dental handpiece of claim 3, wherein said depth is chosen such that the outer peripheral extent of said sleeve means does not substantially exceed the maximum outer peripheral extent of conventional handpieces which do not contain illumination means.

5. The dental handpiece of claim 1, wherein said battery comprises a plurality of axially aligned button-shaped batteries and the diameter of said cavity is only slightly larger than the outer diameter of said batteries.

6. The dental handpiece of claim 5 wherein said body member and said connector each have an additional generally longitudinal bore and each said additional bore communicates with a corresponding end of said cavity for providing a path for fluid through the cavity in the spaces around said batteries.

7. The dental handpiece of claim 1, wherein said body member and said connector each has at least three said longitudinal bores therethrough and said sleeve means has at least two said fluid ducts communicating with respective pairs of said bores.

8. The dental handpiece of claim 7, wherein the transverse cross-sectional area of each of said fluid ducts is substantially equal to the transverse cross-sectional area of one of the pairs of bores communicating therewith.

9. The dental handpiece of claim 1 wherein portions of said body member are electrically insulated from each other and comprise at least a portion of said electrically conductive means connecting said battery means and said illuminating means.

10. The dental handpiece of claim 9 wherein said electrically conductive means comprises portions of said body member, said head member and said connector means and does not include wires.

11. The dental handpiece of claim 2 wherein at least one of said bores has a generally right angle bend at the end thereof communicating with the corresponding one of said ducts.

12. The dental handpiece of claim 2 comprising at least three circumferentially distributed fluid ducts wherein at least one of said ducts is adapted for conveying air and another of said ducts is adapted for conveying water.

13. The dental handpiece of claim 2, wherein said head member comprises an air turbine communicating with at least one of said bores.

14. The dental handpiece of claim 2 wherein said sleeve means comprises a substantially cylindrical inner shell defining said cavity, a substantially cylindrical outer shell surrounding said inner shell and defining therebetween an annular space, and a plurality of longitudinally extending ribs intermediate said shells for dividing said annular space into said plurality of fluid ducts.

15. In a dental handpiece according to claim 1, the said illuminating means comprising a bore in said head member in non-interfering relation with said first mentioned bore and having an open end in proximity to said working tip and said illuminating means comprising an incandescent bulb removably received in said bore with the operative end of said bulb located at said open end and said bulb positioned such that a beam of light from said bulb is directed substantially toward said working tip.

16. The dental handpiece of claim 15, wherein said illuminating means is adapted to direct its light beam such that the axis of the beam of light will intersect the axis of the dental tool at a distance from the head member substantially equal to the average distance from head member to tip of the dental tools most commonly used by dentists in conjunction with dental handpieces.

17. The dental handpiece of claim 15 wherein said bore is a cylindrical bore extending obliquely through said handpiece, said open end in the head member adapted to peripherally engage the said bulb and said bore having a second open end axially spaced from said first mentioned open end and said handpiece further comprising closure means for closing said second open end for retaining therein a bulb inserted in said bore.

18. The dental handpiece of claim 17 wherein said closure means comprises electrical contact means for contacting one terminal of said bulb and the wall of said bore comprises electrical contact means for contacting the other terminal of said bulb.

19. The dental handpiece of claim 1 further comprising resilient electrical contact means for resiliently pressing against that end terminal of said battery which is adjacent said connector, for maintaining electrical contact with said battery.

* * * * *